United States Patent [19]

Cheung

[11] Patent Number: 4,757,017

[45] Date of Patent: Jul. 12, 1988

[54] IN VITRO CELL CULTURE SYSTEM

[75] Inventor: Herman S. Cheung, Waukesha, Wis.

[73] Assignee: MCW Research Foundation, Inc., Milwaukee, Wis.

[21] Appl. No.: 651,392

[22] Filed: Sep. 14, 1984

[51] Int. Cl.$^4$ .............................................. C12N 5/00
[52] U.S. Cl. .......................... 435/240.23; 435/240.24
[58] Field of Search ... 435/240, 241, 948, 240.1–240.31

[56] References Cited

U.S. PATENT DOCUMENTS 3,717,551 2/1973 Bizzini et al. ....................... 435/241

FOREIGN PATENT DOCUMENTS 8304177 12/1983 PCT Int'l Appl .................. 435/240

OTHER PUBLICATIONS

Cheung et al, "Release of Collagenase, Neutral Protease, and Prostaglandins from Cultured Mammalian Synovial Cells by Hydroxyapatite and Calcium Pyrophosphate Dihydrate Crystals", Arthritis and Rheumatism, vol. 24, No. 11, pp. 1338–1344. Nov. 1981.
Akao et al, "Dense Polycrystalline Beta-Tricalcium Phosphate for Prosthetic Applications" Journal of Materials Science 17 pp. 343–346 (1982).
Cheung et al, "Phagocytosis of Hydroxyappatite or Calcium Pyrophosphate Dihydrate Crystals by Rabbit Articular Chondrocytes . . . ", Proceedings of the Society for Experimental Biology and Medicine 173, p. 181–189 (1983).
Chang, "Polymer Implant Materials with Improved X-Ray Opacity and Biocompatibility", Biomaterials 2(3) pp. 151–155 (1981).
Cheung, H. S., M. T. Stony, & D. J. McCarty, 1984 Mitogenic Effects of Hydroxyapatite and Calcium Pyrophosphate Dihydrate Crystals on Cultured Mammalian Cells, Arthritis Rheum. 27:688–674.
Cheung, H. S. and D. J. McCarty, 1984, Biological Effects of Calcium Containing Crystals on Synoviocytes. In Calcium in Biological System, Eds. R. P. Rubin, G. Weiss, and J. W. Putney, Jr. Plenum Publishing Co., N.Y.
Cheung, H. S. & D. J. McCarty, 1983, Calcium Containing Crystals Can Substitute for Platelet Derived Growth Factor (PDGF) in Cell Culture, Arthritis Rheum. 26:S60. (Abstract only).
Evans, R. W., H. S. Cheung, & D. J. McCarty, 1984, Cultured Canine Synovial Cells Solubilize 45Ca Labeled Hydroxyapatite Crystals, Arthritis Rheum. 27:829–832.
Cheung, H. S., P. B. Halverson, & D. J. McCarty, 1982, Release of Collagenase, Neutral Protease and Prostaglandins from Cultured Mammalian Synovial Cells by Hydroxyapatite and Calcium Pyrophosphate Dihydrate Crystals, Arthritis Rheum. 24:1338–1344.
Nery, E. B., K. L. Lynch & G. E. Rooney, 1978, Alveolar Ridge Augmentation with Tricalcium Phosphate, Journal of Prosthetic Dentistry. 40:668–675.
Nery E. G. & K. L. Lynch, 1978, Preliminary Clinical Studies of Bioceramic in Periodontal Osseous Defects, Journal of Periodontology, 49:523–527.
Jarcho, M. 1981, Calcium Phosphate Ceramics as Hard Tissue Prosthetics. Clinical Orthopaedics, 157:259–278.
Evans, R. W., H. S. Cheung and D. J. McCarty, 1983, Uptake and Dissolution of Calcium Phosphate Crystals by Cultured Canine Synovial Cells. Arthritis Rheum. 26:S60.

Primary Examiner—Charles F. Warren
Assistant Examiner—Gail F. Knox
Attorney, Agent, or Firm—Quarles & Brady

[57] ABSTRACT

In vitro cell culture systems for anchorage-dependent mammalian cells using solid substrates of mitogenic calcium compounds, such as hydroxyapatite and tricalcium phosphate forms of calcium phosphate and calcium carbonate. The calcium solid substrates can be in the form of granules with a particle size of at least 0.050 mm. or in the form of solid bodies and may be either porous or non-porous. Unique features of cells cultured in the stated in vitro cell culture systems include the growth of cells in layers many cells thick, growth of cells that maintain their phenotype and the ability to culture cells for extended periods of time.

7 Claims, 12 Drawing Sheets

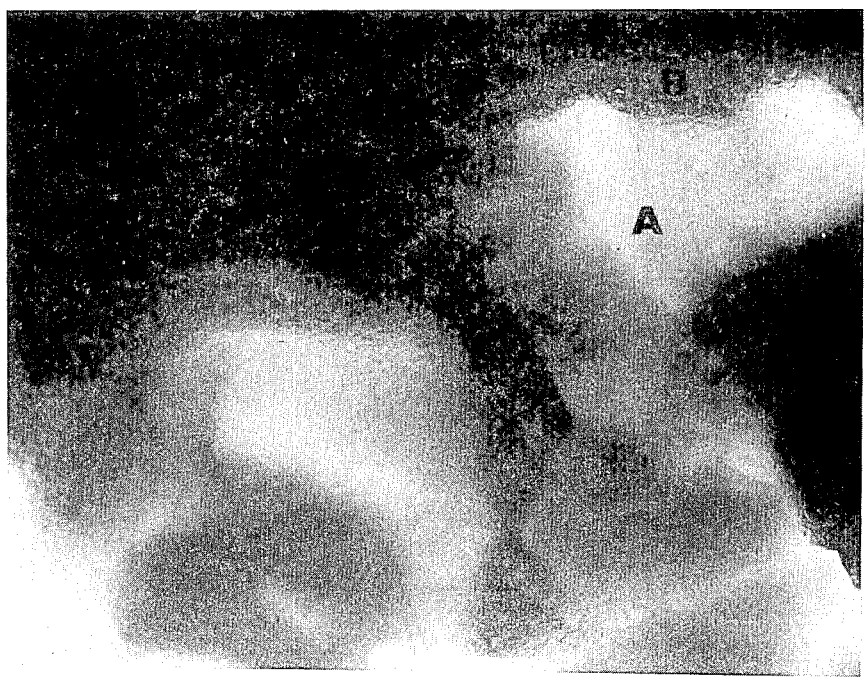
Fig. 7
Fig. 8
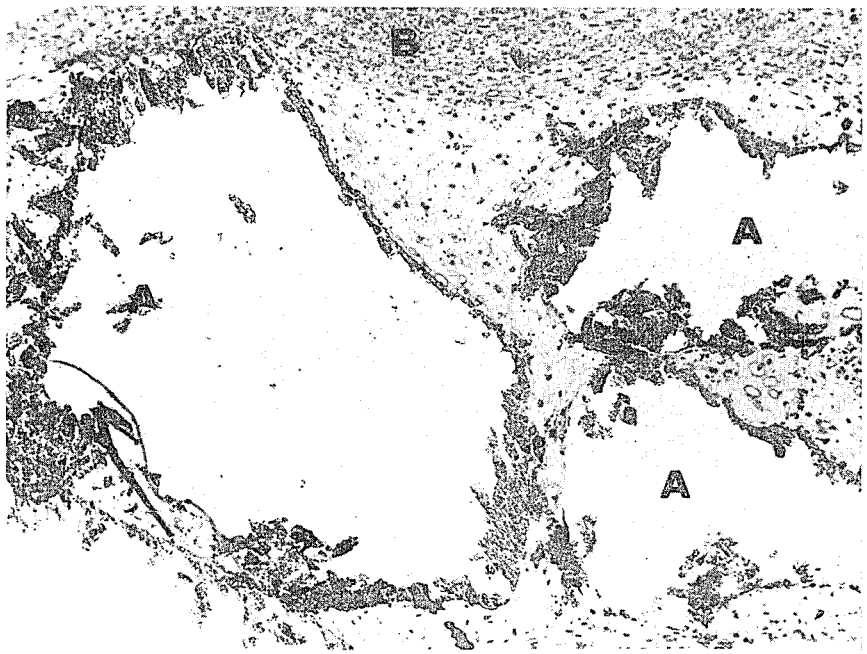

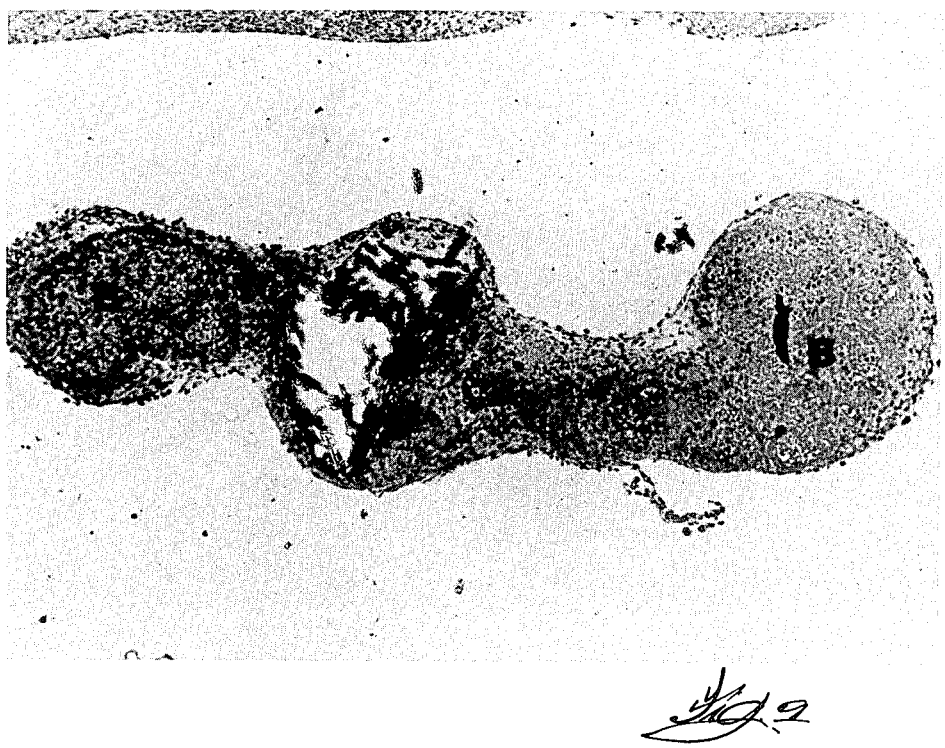
Fig. 9
Fig. 10

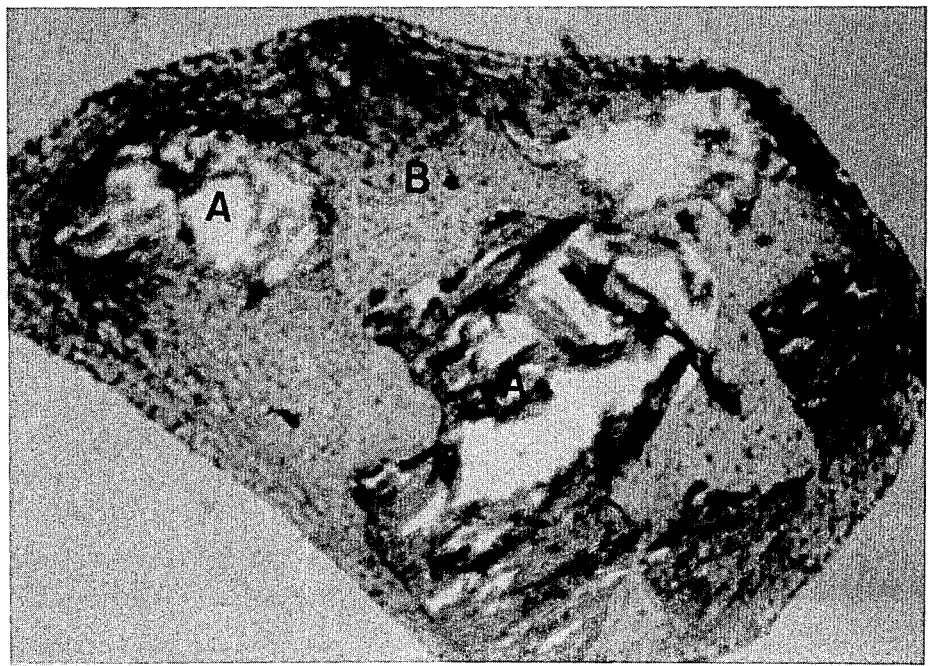
Fig. 11
Fig. 12
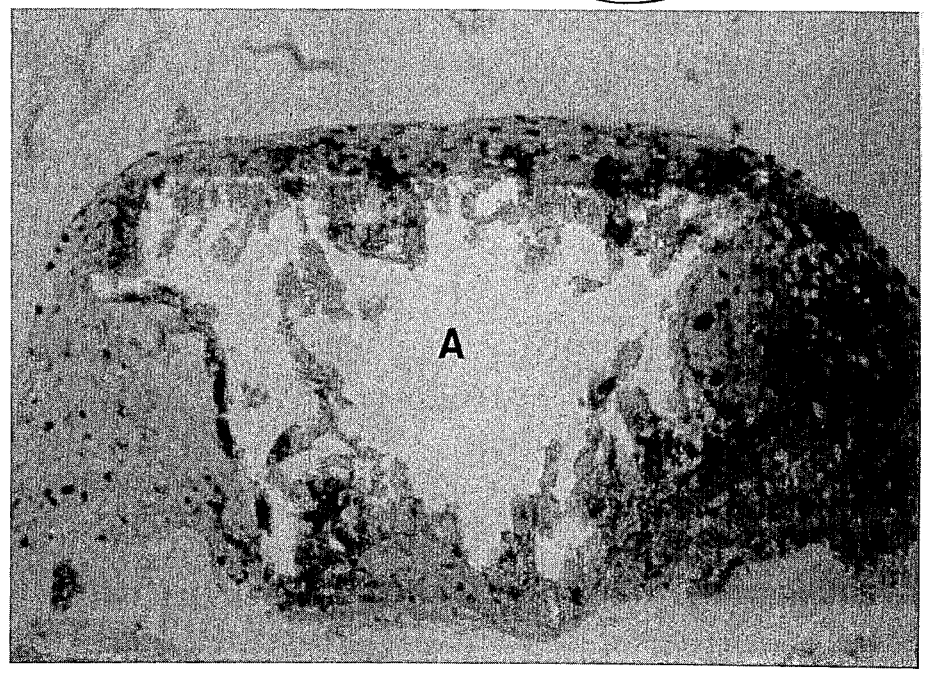

SDS gel electrophoresis profile of collagen produced by (a) cartilage organ culture (b) chondrocytes grown on porous HA granules of Example 1 part (a) and (c) chondrocytes grown on traditional plastic dishes SDS gel electrophoresis profile of cyanogen bromide peptides of α₁ chains isolated from (a) cartilage organ culture, and (b) chondrocytes grown on porous HA granules of Example, 1, part (a).

IN VITRO CELL CULTURE SYSTEM

FIELD

This invention relates generally to the art of growing anchorage-dependent mammalian cells; more particularly, this invention is based upon the discovery that certain substrate materials not heretofore used for in vitro cell culture yield remarkable results not attainable with known solids previously employed for cell culture.

PRIOR ART

In the ensuing description, technical articles are indicated by a reference numeral in parentheses, e.g. (1), and the citations for the articles are listed at the end of the description.

The culture of mammalian cells is biologically important to the scientific community and the pharmaceutical industry for a number of reasons. Research and study of cell structure and morphology are fundamental to continued progress in the diagnosis and treatment of human diseases. Numerous cell products are of vital importance therapeutically and commercially, including hormones, enzymes, viral products, vaccines, interferons, nucleic acids, etc., and require large scale cell culture systems for their production.

Normal and primary diploid mammalian cells can be grown and maintained in vitro but are anchorage-dependent, i.e. they require a solid surface or substrate for growth. The solid substrate is covered by immersed or suspended in a nutrient medium appropriate to the particular cell type to be cultured. The nutrient medium and solid substrates generally are contained in a suitable vessel to which an adequate supply of oxygen and carbon dioxide is furnished in order to support cell growth and maintenance. Cell cultures may be batch systems in which nutrients are not replenished during cultivation but oxygen is added as required, fed-batch systems in which both nutrient and oxygen concentrations are monitored and replenished as necessary, and perfusion systems in which nutrient and waste product concentrations are monitored and controlled.

Anchorage-dependent mammalian cells were grown initially in sealed glass bottles, dishes or other suitable vessels, the glass providing a solid substrate appropriate for cell culture. Plastic vessels replaced glass vessels as the preferred surface for in vitro cell growth since they offered a number of advantages such as reasonableness of price, reduced breakage, and biocompatibility with most types of cells. Roller bottle techniques were developed to increase the surface-to-volume ratio of the vessel and thereby aid large scale cell culture; this method involves rotating plastic or glass bottles to alternately expose the cells to oxygen in the air space of the bottles and to the growth medium contained in the bottles. However, roller bottle systems are said to be cumbersome, expensive in labor and materials, and subject to variations which make it impractical to monitor cellular kinetics and change the growth environment (1).

Other systems were developed to increase the surface-to-volume ratio of the culture vessel or solid substrate as compared to roller bottle systems, such as the multiple propagator, spiral film, plastic bags, gyrogen with tubes, artificial capillaries and tubular spiral film so as to facilitate large scale cell culture. A brief discussion of these systems is set forth in (1). Solid matrix perfusion systems were developed by McCoy et al (2) that utilize glass columns packed with glass beads or helices which form a glass matrix as the solid substrate for cell growth. Once cells have attached to the glass matrix, medium is continuously recycled from a storage vessel. A very similar perfusion system using hollow fibers as the solid matrix instead of glass beads has been developed by Amicon Corporation (3).

Van Wezel discovered and developed the use of very small spheres (microcarriers) as the solid substrate for the culturing of anchorage-dependent mammalian cells (4), (5). His initial work demonstrated the utility of diethylaminoethyl Sephadex (Registered Trademark) A-50, a beaded ion-exchange gel, for this purpose. The microcarriers are kept in suspension in the growth medium by gentle stirring in a suitable vessel. The large surface-to-volume ratio of the microcarrier system provides the potential for high cell yield. Microcarriers of various types are marketed extensively for cell culture by Pharmacia Fine Chemicals AB under its Registered Trademark Cytodex, and they are fully described in a book published by the company (6).

Even though the foregoing cell culture systems are practiced currently to a greater or lesser degree, they all have disadvantages which reduce their effectiveness to less than optimum levels. Systems other than the microcarrier technique are difficult to operate and control; most limit the ability to directly examine and assess the state and progress of the culture such as by microscopic examination, thereby requiring use of measurements such as glucose usage or oxygen uptake as indirect indications of the status of the culture. Microcarrier systems are currently regarded as the most suitable for large scale cell culture since they have the highest surface-to-volume ratio of the foregoing systems and enable monitoring and control. Nevertheless, microcarrier culture systems have a number of serious disadvantages g(1 at pp. 107–108): not all cell lines can be removed from the microcarriers without reducing cell viability; small microcarrier cultures cannot be used to innoculate larger microcarrier cultures, so that a production facility must use other culture systems for this purpose; the cost of microcarriers is high, which can necessitate reprocessing of the microcarriers for reuse with its attendant costs; and the oxygen transfer characteristic of microcarrier systems is rather poor.

Moreover, all of the foregoing cell culture systems have two major shortcomings. First, the cells grow only ga single layer thick—i.e. as a monolayer—on the solid substrate in all of the systems discussed above. This results in a very low cell density per unit area of solid substrate. Second, cells grown in all of the foregoing systems do not, based upon present information, maintain their phenotype; that is, they behave differently biochemically and metabolically than the tissues from which they were derived. Therefore, cells grown in monolayer in vitro culture systems hardly resemble the multicell-layer tissue in vivo. My present invention presents a cell culture system that obviates these disadvantages.

DISCLOSURE OF INVENTION

The cell culture system of this invention involves growing anchorage-dependent mammalian cells on a solid substrate in an appropriate nutrient growth solution in which the solid substrate is a mitogenic calcium compound that is non-toxic to cells in an in vitro culture system. The research that culminated in this invention, the results of which are set forth in detail in the description that follows, demonstrates that cells grown in vitro on an appropriate calcium solid substrate exhibit several novel characteristics.

I. The cells grow many layers thick, instead of growing only as a monolayer.
II. The cells maintain their phenotype, as established by biochemical and histological characterization.
III. Growth of the cells can be maintained in the in vitro culture conditions for long periods of time, at least for times in excess of 11 to 13 months based on present data.

These properties of the new cell culture system of this invention are of singular importance, as explained further below, and are not attainable with presently known in vitro cell culture systems such as those decribed above.

DESCRIPTION OF THE DRAWINGS

The present invention is described below in the detail required by 35 USC §112 as to enable those skilled in the science of cell culture to practice the invention and to set forth the presently-contemplated best modes for its practice by reference to the following drawings.

FIGS. 1-16 relate to Example 1, wherein

FIG. 1 is a scanning electron photomicrograph (SEM) at 50× of the granular solid substrate used in part (a) of Example 1;

FIG. 2 is an SEM at 200× illustrating the cell culture of part (a) after two weeks;

FIG. 3 is an SEM at 500× also illustrating the cell culture of part (a) after two weeks;

FIG. 4 is a transmission electron photomicrograph (TEM) at 20,000× also illustrating the cell culture of part (a) after two weeks;

FIG. 5 is a light photomicrograph at 125× of an H and E stained section of the cell culture of part (a) after four weeks;

FIG. 6 is a light photomicrograph at 200× of a toluidine blue stained section of the cell culture of part (a) after four weeks;

FIG. 7 is a light photomicrograph at 75× of the cell culture of part (a) after eight months;

FIG. 8 is a light photomicrograph at 125× of a toluidine blue stained section of the cell culture of part (a) after eight months;

FIG. 9 is a light photomicrograph at 50× of the cell culture of part (a) after eleven months;

FIG. 10 is a light photomicrograph at 125× of a portion of FIG. 9;

FIG. 11 is a light photomicrograph at 125× of a section of the cell culture of part (a) after thirteen months of growth stained with toluidine blue;

FIG. 12 is a light photomicrograph at 125× of a section of the cell culture of part (a) after thirteen months of growth stained with Safran-0 red stain;

FIG. 13 is a set of sodium dodecyl sulfate (SDS) electrophoresis profiles illustrating collagen typing;

FIG. 14 is a set of SDS electrophoresis profiles illustrating collagen typing by cyanogen bromide peptide analysis.

FIG. 15 is a light photomicrograph at 40× of the cell culture of part (b) of Example 1 after six weeks; and FIG. 16 is a light photomicrograph at 200× of the cell culture of part (b) after twelve weeks.

FIGS. 17 and 18 relate to Example 4, wherein:

FIG. 17 is a light photomicrograph at 125× of the cell culture of Example 4 using a granular solid substrate; and FIG. 18 is a light photomicrograph at 125× of the cell culture of Example 4 using a disc form of solid substrate.

FIGS. 19, 20 and 21 relate to Example 12, wherein:

FIG. 19 is a light photomicrograph at 75× of a cell culture of Example 12 at twelve weeks;

FIG. 20 is a light photomicrograph at 125× of an H&E stained section of a cell culture of Example 12 at twelve weeks; and FIG. 21 is a light photomicrograph at 150× of an H&E stained section of a cell culture of Example 12.

BEST MODES FOR CARRYING OUT THE INVENTION

Figure 1:

The ensuing detailed description sets forth comprehensive experimental data that establish the unique results attained with cell culture systems of this invention.

The novel feature of this invention resides in the discovery that certain calcium compounds provide new and useful results when used as a solid substrate for in vitro cell culture. Examples 1-12 show the effectiveness of several types of these materials for the growth of eleven different types of anchorage-dependent mammalian cells as follows:

Example 1 .... canine articular chondrocytes
Example 2 .... rabbit articular chondrocytes
Example 3 .... human articular chondrocytes
Example 4 .... mouse osteoclasts and osteoblasts
Example 5 .... rabbit osteoblasts
Example 6 .... rabbit periosteal fibroblasts
Example 7 .... canine meniscus fibroblasts
Example 8 .... human foreskin fibroblasts
Example 9 .... mice (CDI) skin fibroblasts
Example 10 .... rabbit synovial cells
Example 11 .... hamster kidney cells.
Example 12 .... canine meniscus fibroblasts In the examples, calcium solid substrates of various types were seeded with cells in a petri dish and covered with a nutrient growth medium appropriate to the particular cell under investigation, following which the cells were cultured under conditions appropriate to the particular cell. Both the nutrient media and the culture conditions for the cells as employed in the examples are the same as used with known cell culture techniques with prior art solid substrate materials; one of the advantages of the present cell culture system is that no special growth conditions or growth medium are required for its practice. Thus, the nutrient growth medium will comprise nutrients, salt solutions, buffers, sera, pH indicators and antibiotics as are appropriate for the specific cell type to be cultured. For most cells, the medium is maintained at a pH in the range of about 7.2 to 7.6.

Various types of mitogenic calcium solids are demonstrated to be useful for in vitro cell culture in the illustrative examples which follow, all of which are mitogenic calcium solids that are very slightly soluble in the nutrient medium and non-toxic to mammalian cells. The specific calcium compounds presently considered most efficacious for the practice of this invention include the hydroxyapatite (HA) form of calcium phosphate, $Ca_{10}(PO_4)_6(OH)_2$; the tricalcium phosphate (TCP) form of calcium phosphate, $Ca_3(PO_4)_2$; and calcium carbonate, $CaCO_3$.

Both hydroxyapatite (HA) and tricalcium phosphate (TCP) can be produced from tribasic calcium phosphate by methods known in the art. Thus, TCP can be made by heating tribasic calcium phosphate to a temperature below its unstable temperature of 875° C. and quickly cooling the material down to room temperature. HA can be made by heating tribasic calcium phosphate to a temperature in the range of 900° C. up to about 1250° C. to yield a material composed of from 72 to 96% HA and the balance TCP, with the proportion of HA increasing with heating at the higher end of the temperature range. In the following examples, HA was prepared starting with commercially-available tribasic calcium phosphate purchased from the T. J. Baker Chemical Co. To prepare the non-porous form of HA, tribasic calcium phosphate powder was compacted into a selected shape in a Reichle press and sintered at 1100° C. To prepare the porous form of HA, tribasic calcium phosphate powder was mixed with napthalene particles of about 500 micron average size, compacted in a Reichle press and heated in a Globar furnace at 400° C. for four hours to sublimate and remove the napthalene and thereby produce a porous material; the porous material was thereafter sintered for 8 hours at 1100° C. Both the porous and non-porous forms of Examples 1–11 when analyzed by energy dispersive analysis comprised about 90% HA and the balance TCP, with an average molar ratio of calcium to phosphate of about 1.60. Granules of these materials are used in some of the examples; the materials were ground by hand and sieved to a particle size in the range of about 0.1 to 0.5 millimeters to prepare the granules. Methods for sintering calcium phosphate and producing porous forms thereof are known in the art and described in the literature (1, 7, 8).

Calcium carbonate suitable for the present cell culture systems is available from numerous companies and can be prepared by various known techniques. The calcium carbonate used in Example 12 was a commerically-available granular grade produced from high calcium calcitic limestone quarried from underground mines, but calcium carbonate made from other starting materials also can be used.

Before use, the calcium solids were ultrasonically cleansed, sterilized at 121° C. for 30 minutes in an autoclave, washed twice for five minutes each time with the specific culture medium to be used in a particular example to remove any extra debris, and stored in the medium until used for cell culture.

In the photomicrographs of the drawings referred to in the examples, various areas are marked with a reference letter as follows:
A=solid substrate of a calcium compound;
B=cells;
C=alcian blue stained areas;
F=fibrils;
G=glycogen; and
N=nucleus.

EXAMPLE 1

Hyaline cartilage is a specialized connective tissue whose major function depends on the state of hydration and the structural arrangement of a vast extracellular matrix. As a tissue, cartilage is characterized by a rather homogeneous cell population, which cells produce structural macromolecules (e.g., type II collagen and cartilage-specific proteoglycan) that are the biochemical expressions of the cell's phenotype. The chondrocyte establishes a specialized microenvironment, the territorial matrix, and in contrast to the majority of cells found in other tissues, exists without direct cell-cell contact. Each cell can be thought of as a functional unit of cartilage and, as such, is ultimately responsible for the turnover of the extracellular matrix of the entire tissue.

Mammalian chondrocytes have been isolated for culture from different cartilages (9,10,11,12). As noted above, chondrocytes produce two well characterized structural macromolecules that have been used to define their specific differentiated phenotype, cartilage proteoglycan and type II collagen. However, when chondrocytes from avian and mammalian species are released from the cartilage matrix and grown in monolayer cell culture systems, they stop producing these characteristic molecules in a variety of situations (13–19). The collagen phenotype of the progeny of a cloned chondrocyte has been shown to change from type II to type I and type I trimer collagen during growth to senescence (20). This observation has been verified with mass cultures and expanded to describe a complex dedifferentiated phenotype of collagen types I, I trimer, III and V (21,22).

In this example, evidence is presented showing that isolated canine articular chondrocytes establish a tissue-like matrix in vitro without alterations in their biochemical phenotypic expression when grown, according to the present cell culture system, on a solid substrate consisting of the method of isolation and the culture characteristics of these porous hydroxylapatite (porous HA). A morphologic appearance study of these chondrocytes is described, and a biochemical study is presented to compare the collagen synthesized by these cells to the cartilage from which they were isolated.

Materials and Methods. All culturing medium such as Dulbecco's Modified Eagle Medium (DMEM) with high glucose (4.5 g/liter), horse serum (HS) and penicillin-strepomycin-fungizone (PSF) mixture were obtained from M.A. Bioproducts (Walkerville, Md.).

Pepsin (PM grade) collagenase (type II), and trypsin were purchased from Worthington Biochemicals. Reagents for SDS electrophoresis were purchased from Bio-Rad Laboratory. Aquasol and [2,3,$^3$H] proline (30–50 Ci/mMol) were obtained from Amersham (Arlington Heights, Ill.). Falcon culture plates were from Becton-Dickerson (Oxnard, Calif.).

Part (a).

For this part of Example 1, porous HA was used as the solid substrate for the cell culture. The HA was ground into granulated form with a mortar and pestle and sieved to uniform size (about 500 microns) with a sieve.

(1) Cell culture: Normal canine cartilages were used. Cartilage slices were removed from the femoral condylar surfaces and placed immediately in Hank's Balanced Salt Solution (HBSS) at room temperature. Chondrocytes were enzymatically released from cartilage according to the procedure of Cheung and Ryan (23).

The released cells were suspended in growth medium consisting of DMEM supplemented with 10% (v/v) horse serum and 1% (v/v) PSF. Approximately $5 \times 10^5$ cells were seeded on 500 mg of the porous HA granules in 60 mm$\times$15 mm petri dishes. Four ml of growth medium was added per dish and the cultures were maintained in a $CO_2$ incubator (Forma Scientific, Marietta Ohio), with replacement of medium twice a week. By the end of the second week, the calcium granules were usually completely covered with cells. For biochemical and morphological studies, some of these cultures were maintained for more than 13 months.

(2) Light microscopy and scanning electron microscopy: Samples were prepared for both light microscopy and scanning electron microscopy. Light microscopic samples were imbedded in JB-4 imbedding medium and were sectioned on a microtome equipped with a carbide steel knife. Samples for scanning electron microscopy underwent critical point drying with $CO_2$; each specimen was mounted and coated with carbon and gold-palladium in a Denton DV 520 vacuum chamber. Specimens were examined on an Amray Model 1200 scanning electron microscope at 15–25 kilovolts.

(3) Collagen labelling and purification: For biosynthetic studies, the HA granules with cells were labeled in 4 ml of DMEM containing $^3H$ proline (50 micro Ci/ml), L-Ascorbic acid (50 microgram/ml), $\beta$-aminopropionitrate ($\beta$APN) (125 microgram/ml), 10% HS, and 1% PSF. After 24 hours of incubation, the granules were separated from the medium and pulverized with a freeze-mill. They were then extracted with 4 ml of 1 M NaCl/0.05 M Tris buffer, pH 7.5 at 4° C. for 24 hrs. Phenylmethylsulfonyl fluoride (PMSF) and mercaptoethanol were added to inhibit any protease activities. After extraction, they were centrifuged and the insoluble HA residue was discarded. The supernatant was added back to the original medium.

Medium and HA extract were acidified to pH 3.5 with glacial acetic acid and pepsin was added to a final concentration (0.1 mg/ml). The mixture was digested by shaking for 48 hours at 4° C. and was lyophilized. The pepsin was inactivated by dissolving the lyophilized sample in 5 ml cold 0.05 M Tris (pH 7.4) with 1 M NaCl, and the collagen was extracted into this neutral salt solution for 24 hours at 4° C. with gentle shaking. One mg of acid-soluble rat skin collagen was dissolved in the sample. The collagen was then purified by neutral and acid salt precipitation. The precipitate was dissolved and dialyzed extensively against 0.5 N acetic acid. Collagen typing was done with SDS polyacrylamide gel electrophoresis.

The identities of collagen types I, II and III were further established by electroelution and cyanogen bromide (CNBr) peptide analysis. Samples of collagen were prefractionated on 5% gels, sliced, and maintained at 4° C. in a moist environment until the exact positions of the $\alpha_1$ (I) and $[\alpha_1(III)]_3$ were determined by the staining of a replicate gel. The $\alpha$ chains from slices of each fraction were eluted off by electroelution.

The CNBr cleavage of the $\alpha$ chain was performed according to the procedure of Miller (24). The resulting peptides were subjected to SDS polyacrylamide gel electrophoresis.

(4) Results; morphological studies. FIG. 1 is a scanning electron photomicrograph (SEM) at 50× of the porous HA granules A before being seeded with cells; the porous nature of the granules and the nature of their surface configuration is readily apparent.

Figure 2:
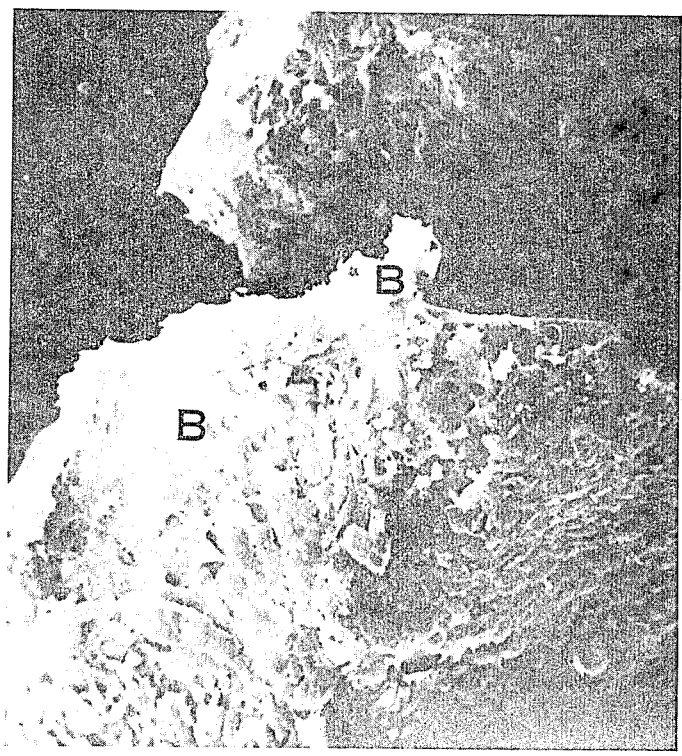
Figure 3:
Figure 4:
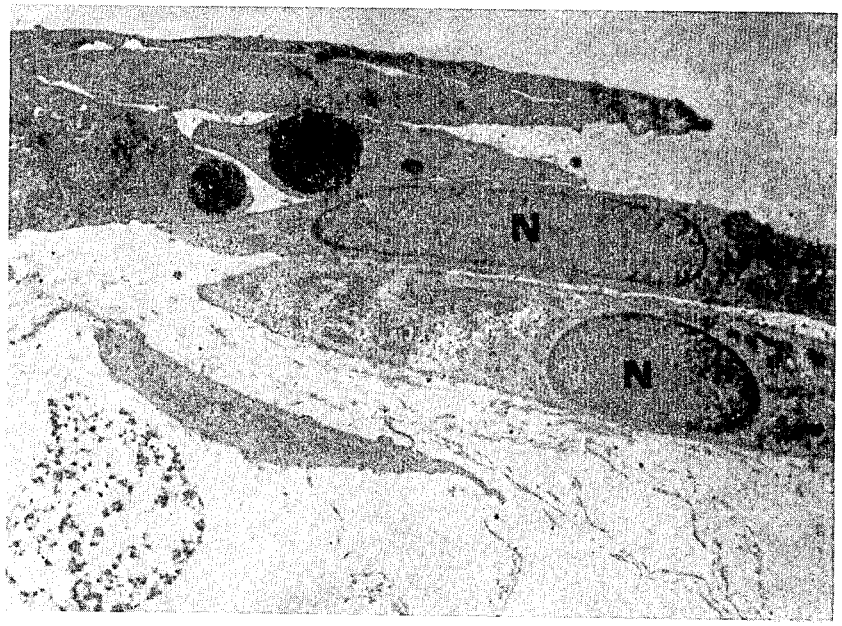

After two weeks of culture, chondrocyte cells B completely covered the surface of the granules A as illustrated in FIG. 2, an SEM at 200× and FIG. 3 an SEM at 500×. Transmission electron microscopic (TEM) examination of the culture after two weeks revealed large intracellular glycogen droplets G, which are typical of canine chondrocytes, and extracellular collagen fibrils F are also evident as shown in FIG. 4, a TEM at 6,200×.

Figure 5:
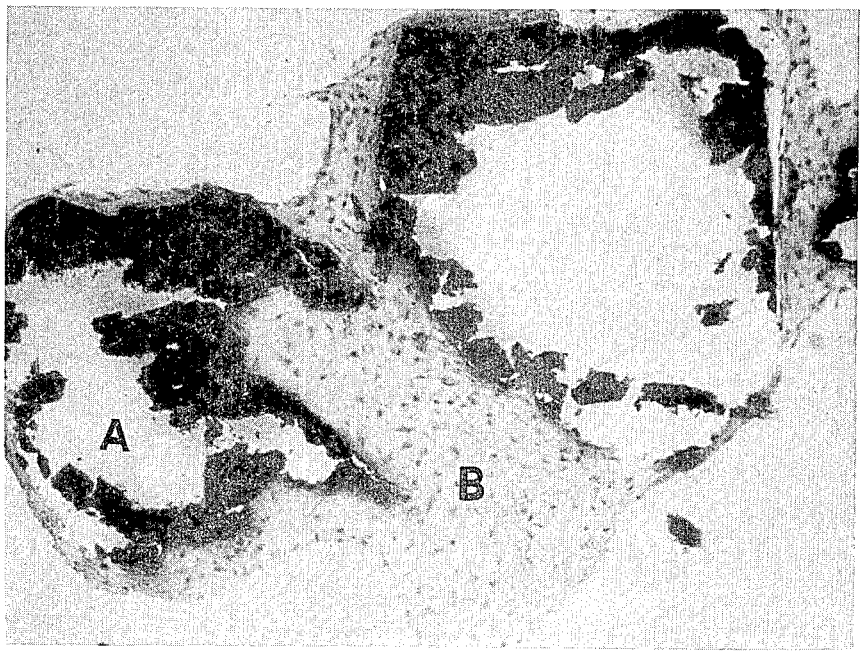
Figure 6:
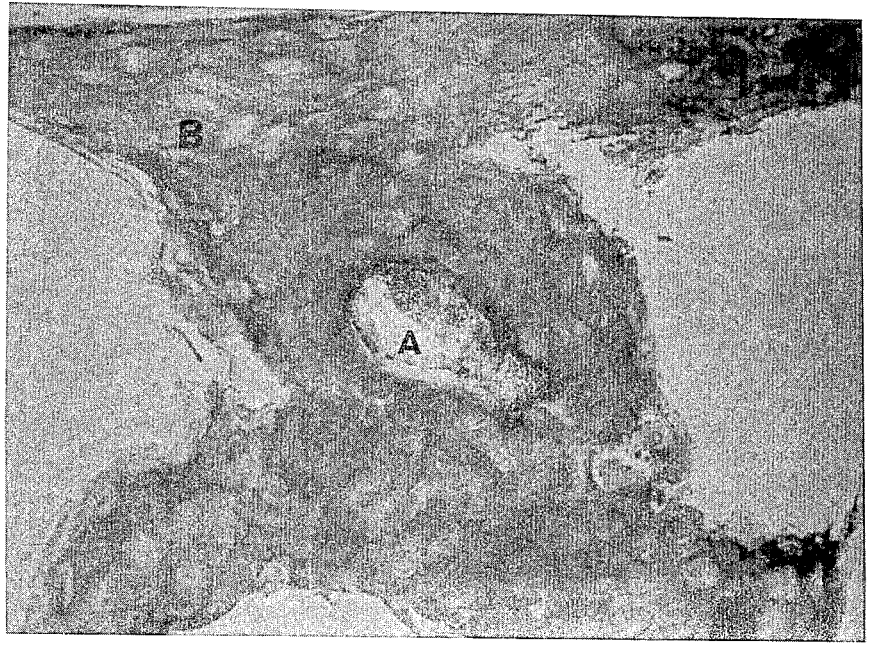

After four weeks of culture, some of the calcium granules with their attached cells were removed from the culture dish, cross-sectioned, stained and examined under a light microscope. FIG. 5 is a photomicrograph at 125× of an H and E stained section. Individual cells B appear as dark spots on the photomicrograph. It can be seen in FIG. 5 that the cells have multiplied and grown in a multi-cell layer form on the surface of the granules B. The granules A appear as white areas surrounded by dark boundaries in FIG. 5 because they become gouged out when sectioned. Another section of the culture at this stage was stained with toluidine blue stain, which is specific for acid proteoglycan, a compound found in cartilage matrix formation. FIG. 6 is a light photomicrograph at 200× of an toluidine blue stained cross-section in which the intercellular zones such as indicated by the reference letter C were very densely stained in a dark bluish or purplish color, thereby demonstrating the formation of acid proteoglycan within these areas.

The cell culture of this example was examined again after eight months of growth. FIG. 7 is a light photomicrograph at 75×, and it will be noted that the cell layers B on the granules A are almost as thick as the diameter of the granules themselves and resemble cartilage in appearance. This tissue was also stained very heavily with toluidine blue stain. FIG. 8 is a light photomicrograph at 125× of the stained cross-section, in which the areas such as indicated with the reference letter C are heavily stained and appear dark bluish or purplish in the original colored photomicrograph.

The cell culture was examined again after eleven months of growth. FIG. 9 is a light photomicrograph at 50× of the culture at this stage, and it will be noted that the cells B have continued their growth and differentiation throughout this long period of time. FIG. 10 is a light photomicrograph at 125× illustrating an enlarged view of the left hand section of FIG. 9 to further emphasize the multiple layers of cells B grown on a granule of substrate A.

FIGS. 11 and 12 are light photomicrographs of the cell culture after 13 months of growth. FIG. 11 illustrates a section of the cell culture stained with toluidine blue at 125× magnification in which the blue staining demonstrates matrix formation characteristic of the cartilage cells. The section of FIG. 12 is also at 125× magnification but is stained with safran-0 red stain; the red stain is specific to chondroitin sulfate which is a major component for cartilage matrix. The blue stain of FIG. 11 also shows the presence of the same compound, but the red stain of FIG. 12 is more specific to the compound. FIGS. 11 and 12 demonstrate that the cartilage cells grown with the present invention maintain their phenotype for up to as long as 13 months. The cell culture was terminated at the end of 13 months of growth, but it could have been continued for an even longer time.

Figure 13:
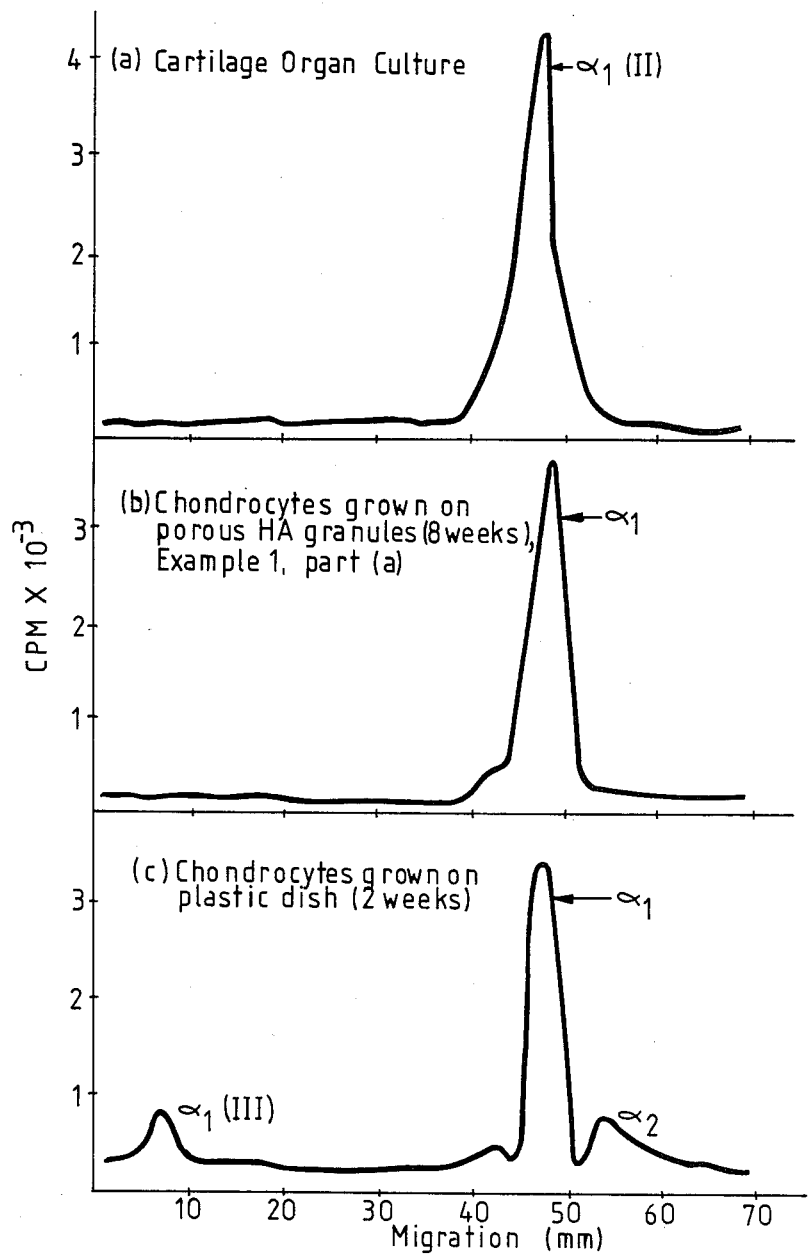

(5) Results—biochemical studies. FIG. 13 illustrates the profile, determined by sodium dodecyl sulfate (SDS) gel electrophoresis, of collagen from three different sources:

Profile (a)—collagen from cartilage organ culture, which is identified as type II;

Profile (b)—collagen synthesized by chondrocytes cultured on porous HA according to this example, at eight weeks; and Profile (c)—collagen synthesized by the same chondrocytes used in this example but cultured on plastic dishes, at two weeks.

Profile (a) represents the profile of collagen from natural tissue. Profile (b) represents the profile of collagen synthesized by chondrocytes cultured according to this invention, and it can be seen that the curve is almost exactly the same as Profile (a). Profile (c) represents the profile of collagen synthesized by cells grown by a prior art cell culture system; it will be noted that these cells synthesized a mixture of type I, type II and type III collagens and that Profile (c) does not resemble Profile (a).

Figure 14:
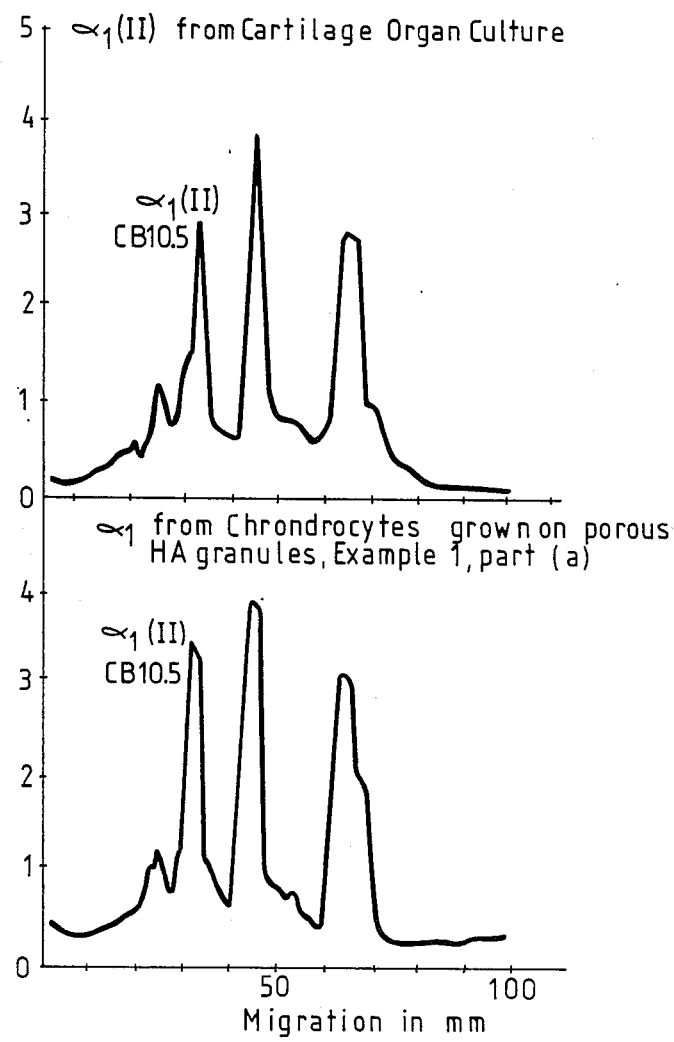

Collagen identities of Profiles (a) and (b) were further confirmed with CNBr cleavage and analyzed on 15% SDS gels. The Profiles of the main peak of these two Profiles of FIG. 13 are shown in FIG. 14. CNBr peptide 10 and 5, which are marker peptides for type II collagen, appeared as prominent peaks in all of the samples grown on HA granules according to this Example (Profile (b) of FIG. 14) and closely resembled the profile (Profile (a) of FIG. 14) of the natural tissue. By contrast, however, $\alpha_1$ peaks from monolayer chondrocytes are a mixture of type I and type II collagen.

Part (b).

Figure 15:
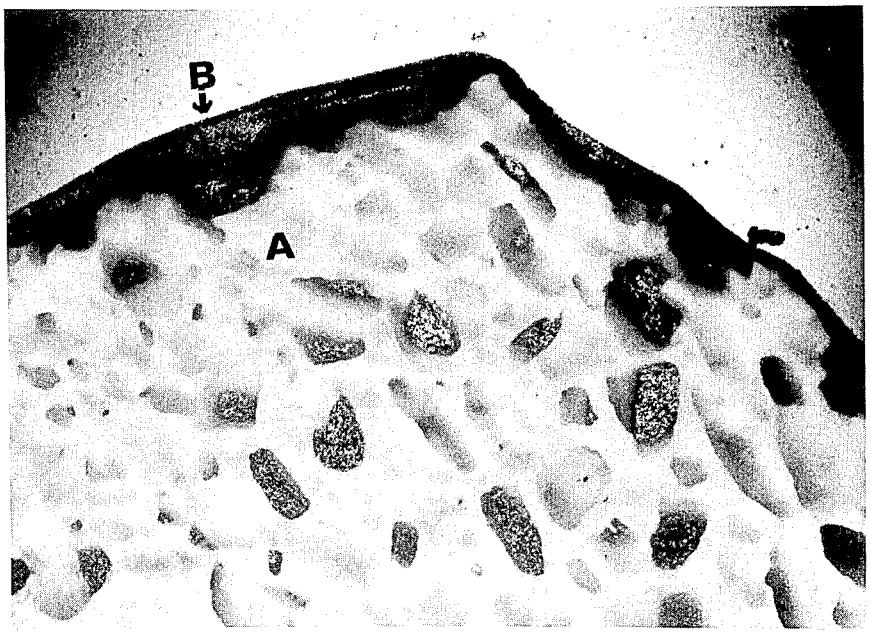
Figure 16:
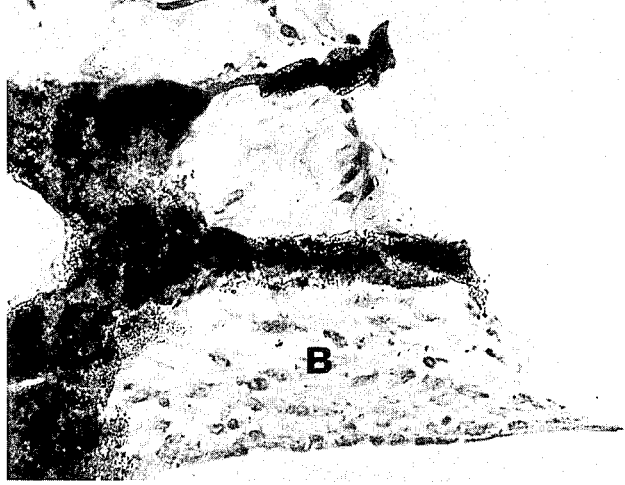

In this second part of Example 1, discs 7 mm in diameter and 1 mm thick were made by fusing by sintering (as previously described) granules of HA with 3 different sizes of napthalene particles having diameters of 100 microns, 500 microns and 1,000 microns. The same cells and all other materials and culture conditions as in part (a) were utilized. Approximately $5 \times 10^5$ chondrocyte cells were seeded onto 6 such discs made with the 500 micron napthalene particles in each 60 mm×15 mm petri dish. The pore size of the discs averaged about 300–500 microns. FIG. 15, a light photomicrograph at 40× taken after 6 weeks of growth shows a portion of a disc A, and it will be noted that the cells B have grown many layers thick about the boundary of the disc and also within the pores about the surface of the disc. FIG. 16 is a light photomicrograph at 200× taken after 12 weeks of growth of a cross section of a disc that illustrates the manner in which the cells B have grown many layers thick in pores of the disc A. Discs made with the 100 and 1,000 micron napthalene particles yielded the same results when used as a solid substrate for cell culture. The cell growth on the discs of part (b) was the same in all respects as cell growth on the granules of part (a), except that there was a greater number of cells per unit weight of substrate with the granules as compared to the discs. It is estimated that cell density per unit weight of substrate when cultured on the granules as in part (a) is about 1,000 times that when cultured on the discs as in part (b). Thus, granules as part (a) would be the substrate of choice in most instances.

EXAMPLE 2

Rabbit articular chondrocyte cells were cultured on the same HA granules and HA discs used in Example 1. The growth medium was DMEM supplemented with 10% fetal calf cerum (FCS) and 1% PSF. The cultures were maintained for 9 months for the granules and for 10 weeks with the discs, following which both light microscopy and SEM were performed. The results were as follows:

(a) Granules—the cells grew as multiple layers on the granules. Biochemical studies showed that only type II collagen was produced by the cells.

(b) Discs—the cells multiplied and migrated into the interior of the porous disc. A multilayer of cell tissue was observed by the third week. Autoradiograph with $^{35}SO_4$ and $^3H$ proline showed heavy cartilaginous matrix formed. H and E and toluidine blue stains confirmed this observation.

EXAMPLE 3

Human articular chondrocyte cells were cultured on the same HA granules and HA discs used in Example 1. The growth medium was DMEM supplemented with 10% FCS and 1% PSF. Both forms of culture were maintained for 15 week. The cells grew more slowly on both forms of solid substrates in comparison to the cells of Examples 1 and 2. Cell layers approximately 3 to 4 cells thick were formed after 10 weeks of culture; when stained with toluidine blue stain, cross sections of the cultures were stained in a dark bluish or purplish color, indicating the formation of cartilaginous matrix.

EXAMPLE 4

Bone tissue is composed of two major compartments, the cellular and extra-cellular constituents. The latter compartment consists of a calcified organic matrix which dominates the tissue in terms of volume, but whose formation and destruction are under the control of the cellular compartment. The cellular compartment contains a variety of differentiated cells that probably differ in origin and in function.

Isolation and primary culturing of different populations of bone cells have been successfully attempted. However, these bone cell cultures can be maintained for only a short period of time (up to 2 weeks) before losing their phenotypic expression.

This example presents evidence indicating that isolated mouse osteoclasts and osteoblasts can form a tissue matrix in vitro without alteration in their biochemical phenotypic expression in cell culture systems of this invention at least for as long as 10 weeks. Biochemical measurements described below include alkaline and acid phosphatase activities, response to parathyroid hormone stimulation, collagen and hyaluronate synthesis.

(1) Materials and methods. The culturing medium for this Example was Earle's Minimum Essential Medium (EMEM) with high glucose (4.5 g/liter), supplemented with 10% (v/v) horse serum (HS) and 1% (v/v) penicillin-streptomycin-fungizone (PSF); all of these were obtained from M.A. Bioproducts (Walkerville, Md.).

Pepsin (PM grade) collagenase (type II), and trypsin were purchased from Worthington Biochemicals. Reagents for SDS electrophoresis were purchased from Bio-Rad Laboratory. Aquasol and [2,3,$^3$H] proline (30–50 Ci/mMol) were obtained from Amersham (Arlington Heights, Ill.). Falcon culture plates were products of Becton-Dickerson, Oxnard, Calif.).

Two forms of porous HA solid substrates were used for the cell cultures of this example: (1) HA granules sieved to a uniform size of about 500 mircons, and (2) HA discs about 7 mm in diameter and 1 mm thick. These are the same substrates used in parts (a) and (b) respectively of Example 1. Before use, the substrates were ultrasonically cleansed and sterilized at 121° C. for 30 minutes in an autoclave.

(2) Cell culture. Osteoclast (OC) and osteoblast(OB) cell populations were obtained by limited sequential enzymatic digestion of neonatal mice (CD-1) calvaria as described by Luben et al (25). OC and OB cells consisted, respectively, of cells released in the second and third (population 2 and 3) and in the fifth and sixth (population 5 and 6) periods of digestion.

Growth conditions were similar to those used in Example 1, except Earle's Minimum Essential Medium (EMEM) was used instead of DMEM.

In the biochemical studies, concurrent cultures of OB and OC cells grown on traditional plastic dishes (Falcon Dish) were used to compare to those grown on granulated HA.

(3) Biochemical assays. Alkaline and acid phosphatase were done according to the method outlined by Wong and Cohn (29). To examine hyaluronate synthesis, the OC and OB cells were labeled in the presence of $^3H$ glucosamine (2 micro Ci/ml) for 24 hours. Purification and measurement of hyaluronate production were done according to the procedure of Cheung et al (26).

To measure synthesis of collagen, both OC and OB cells were labeled in 5 ml of EMEM containg $^3H$ proline (10 micro Ci/ml), Vitamin C (50 micrograms/ml), BAPN (100 micrograms/ml), 10% FCS and 1% PSF.

After 24 hours of incubation, the cell layers were separated from the medium and trypsinized, and a cell count was taken with a hemocytometer. Cells were sonicated and returned to the medium. Three aliquots of 0.5 ml each were removed from both OB and OC cells. Each aliquot was then diluted to 2 ml with a solution containing 1% NaCl and 50 mM Tris HCl (pH 7.5), and was dialyzed extensively against the same buffer at 4° C. The nondialyzed counts were used as an approximation of total collagen and non-collagen protein synthesis, (27).

Collagen was measured as the radioactivity rendered and soluble by purified bacterial collagenase, (28). The radioactivity remaining after collagenase digestion were used as non-collaginous protein.

(4) Results. Table I summarizes acid and alkaline phosphatase activities of OC and OB cells grown on plastic petri dishes and HA granules. Phosphatase activities and the ratio between the two phosphates are similar with both types of solid substrates after 1 week of culture. The value of lines (1) and (4) of Table I are comparable to those reported by other investigators (26). However, after 10 weeks of culture, cells grown on the HA granules still maintained similar levels of phosphatase activities, see lines (3) and (6) of Table I, thereby showing they still maintained their phenotypic expression. In contrast, concurrent cultures on the plastic dishes died off after only three weeks in culture. Furthermore, Luben et al. (25) have reported that the acid phosphatase/alkaline phosphatase ratio decreases rapidly after one week of culture in plastic dishes; in other words, they lose their phenotypic expression.

Table II summarizes hyaluronate and collagen production by OC and OB cells grown on plastic petri dishes and HA granules. At one week, their values were similar, regardless of culturing substrate, as shown by lines (1), (2), (4) and (5). However, cells grown on HA granules maintained the same level of hyaluronate and collagen production after 10 weeks of culture, as shown by lines (3) and (6). In contrast, cells grown in plastic dishes began to die off after 2 weeks. The levels of hyaluronate and collagen production of all cultures were comparable to published data (29, 30).

Collagen constitutes about 5% of total protein synthesized in OC cells and approximately 12% on OB cells grown in ceramics after one week and 10 weeks (data not shown). Again, values are similar to reported values, (29).

Figure 17:
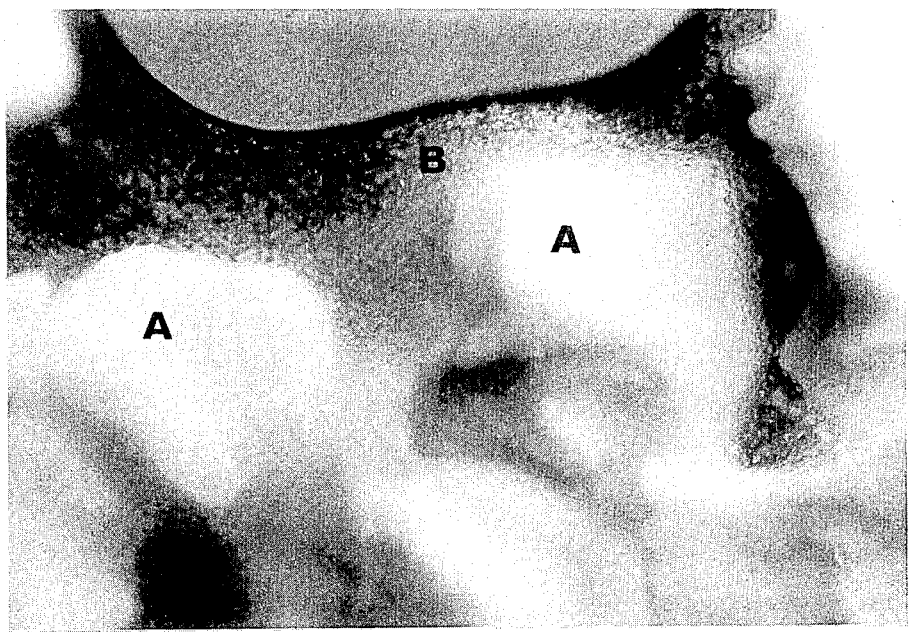
Figure 18:

Light microscopic examination of OC and OB cell cultures on HA granules showed multi-layers of cells grown on the surface of the granules after 24 weeks of culture, FIG. 17. OC and OB cells cultured on the HA discs also developed multilayers of cells on the surface and, in addition, migrated and grew into the pores of the discs, as illustrated in FIG. 18, a photomicrograph taken after 10 weeks of culture.

TABLE I

Phosphate Activity by OC and OB Cells.

| | Cell Type | Growth Substrate | Time in Culture (weeks) | Phosphatase nmol substrate cleaved $10^5$ cells/minutes Acid | Alkaline | Acid/Alkaline Ratio |
|---|---|---|---|---|---|---|
| (1) | OC | Plastic | 1 | 2.1 ± 0.3 | 0.5 ± 0.1 | 4.2 |
| (2) | OC | HA granules | 1 | 2.4 ± 0.2 | 0.6 ± 0.1 | 4.0 |
| (3) | OC | HA granules | 10 | 2.9 ± 0.4 | 0.6 ± 0.1 | 4.8 |
| (4) | OB | Plastic | 1 | 1.5 ± 0.2 | 0.7 ± 0.1 | 2.1 |
| (5) | OB | HA granules | 1 | 1.7 ± 0.1 | 0.8 ± 0.1 | 2.1 |
| (6) | OB | HA granules | 10 | 1.9 ± 0.3 | 0.8 ± 0.3 | 2.2 |

TABLE II

Hyaluronate and Collagen Synthesis by OC and OB Cells

| | Cell Type | Growth Substrate | Time in Culture (weeks) | Hyaluronate Synthesis dpm/$10^6$ cells | Collagen Synthesis dpm/$10^6$ cells |
|---|---|---|---|---|---|
| (1) | OC | Plastic | 1 | $(1.22 ± 0.13) \times 10^5$ | $(3.1 ± 0.3) \times 10^5$ |
| (2) | OC | HA granules | 1 | $1.41 ± 0.21 \times 10^5$ | $(4.0 ± 0.5) \times 10^5$ |
| (3) | OC | HA granules | 10 | $(1.53 ± 0.24) \times 10^5$ | $(4.4 ± 0.5) \times 10^5$ |
| (4) | OB | Plastic | 1 | $(6.3 ± 0.1) \times 10^4$ | $(8.2 ± 0.7) \times 10^5$ |
| (5) | OB | HA granules | 1 | $(7.2 ± 0.2) \times 10^4$ | $(9.6 ± 0.6) \times 10^5$ |
| (6) | OB | HA granules | 10 | $(6.9 ± 0.3) \times 10^4$ | $(10.3 ± 0.3) \times 10^5$ |

EXAMPLE 5

Rabbit osteoblast (OB) cells were cultured with both the HA granular forms and disc forms as used in Example 1. The growth median was EMEM supplemented with 10% (v/v) FCS and 1% (v/v) PSF. The cell cultures were maintained for 10 weeks. Multi-cell layers of tissue were observed with both the granular and disc forms of solid substrate. Analysis showed that the OB cells of both cultures produced only type I collagen, thereby indicating the cells maintained their phenotype. von Kassa stain failed to reveal any calcification in the multicell layer tissues.

Examples 6–9 demonstrate the in vitro culture of fibroblast cells with the solid substrates according to this invention. Both the granular and disc forms of HA as used in Example 1 were used in Examples 6 and 8, and only the granular form of HA as in Example 1 was used in Examples 7 and 9. The growth medium was DMEM fortified with 10% (v/v) FCS and 1% PSF in Examples 6 and 8, and DMEM fortified with 10% (v/v) horse serum and 1% (v/v) PSF in Examples 7 and 9. The results are summarized as follows.

EXAMPLE 6

Rabbit periosteal fibroblast cells were cultured for a period of 10 weeks. The cells were fed twice each week. Light microscopy of the cultures showed: (a) the cells filled the porous interior of the disc form of the HA substrate and grew as a multi-cell layer on the surface of the discs by 5 weeks, and (b) the cells formed multi-cell layers on the surface of the HA granules within 2 weeks. The multi-cell layers continued to grow thicker throughout the 10 week culture period.

EXAMPLE 7

Canine meniscus fibroblast cells cultured on HA granules formed multi-cell layers within 2 weeks and the layers continued to grow thicker throughout the 8 week period for which the culture was maintained. Further, the cells continued to secrete meniscus collagenase into the culture medium throughout the entire 8 week period. In contrast, concurrent culture of the same cells under the same conditions but using plastic petri dishes as the substrate stopped secretion of this enzyme after one week in culture.

EXAMPLE 8

Human foreskin fibroblast cell cultures were maintained for 10 weeks with the disc form of HA substrate and for 6 months with the granule form of HA substrate. The cells grew extremely well on both forms of substrates. Multi-cell layers of cells were observed by the end of the first week and continued to increase in thickness throughout the culture periods. Collagen synthesis per mg cell protein was nearly two-fold greater than that obtained with the same cells grown under the same conditions with plastic petri dishes as the substrate.

EXAMPLE 9

Mice (CDI) skin fibroblast cells were cultured for 5 weeks. The cells grew extremely well on the HA granules. Multi-cell layers formed on the granules by the end of the first week and continued to increase in thickness throughout the culture period. The biosynthetic rate of protein production (measured by the uptake of $^3$H glycine into TCA precipitable fraction) of the cell cultures of this Example was twice that of the same cells grown on plastic petri dishes.

Examples 10 and 11 illustrate the growth of additional types of cells on the solid substrates of this invention.

EXAMPLE 10

Rabbit synovial cells were cultured on both the HA granules and HA discs of Example 1. The growth medium was DMEM fortified with 10% (v/v) FCS and 1% (v/v) PSF. The cultures were maintained for 10 weeks, and were fed twice a week. Light microscopy and histology were performed. Multicell layers grew on the surfaces of both forms of HA substrates; the layers were evident by the second week of culture and continued to increase in thickness throughout the 10 week period. Synovial cells and fibroblast cells appeared to grow the fastest.

EXAMPLE 11

Baby hamster kidney cells (BHK-21, purchased from American Type Culture Collection, Rockville, Md., U.S.A.) were grown on the HA granules of Example 1 using a growth medium of EMEM fortified with 10% (v/v) FCS and 1% (v/v) PSF. The culture was maintained for 4 weeks. Again, multi-cell layers formed about the surface of the granules by the end of the second week and continued to increase in thickness throughout the 4 week culture period.

EXAMPLE 12

Other of my research work (expected to be published in the near future) has shown that canine meniscus fibroblast cells grown in organ cultures secrete a tissue specific neutral proteolytic enzyme-collagenase. Primary cell cultures derived from meniscus when grown on plastic dishes as the solid substrate, a typical prior art technique, retain their phenotypic expression, i.e. by secreting the proteolytic enzyme-collagenase for a period of up to only two weeks, after which the phenotypic expression ceases due to the cells becoming confluent; secondary passaged cells when grown on plastic dish solid substrates, however, do not produce the proteolytic enzyme-collagenase and therefore do not retain their phenotypic expression.

This example demonstrates the efficacy of calcium carbonate as a solid substrate for in vitro cell growth and establishes that cells grown on this substrate will maintain their phenotypic expression for extended periods of time.

The solid substrate used for the cell cultures of this example comprised calcium carbonate granules produced by Omya Inc. (Proctor, Vt. 05765). Chemical analysis of the calcium carbonate established that the granules comprise 98% calcium carbonate, 1% magnesium carbonate and 1% other acid-insoluble elements. The granules were washed extensively with distilled water, following which the water was removed from the granules with 95% ethanol and acetone washes. The granules were then air dried and sieved, and granules with a particle size larger than 0.05 mm. (and an upper particle size of about 0.10 mm.) were employed as the solid substrate in this example. The granules were ultrasonically cleansed, sterilized at 121° C. for 30 minutes in an autoclave, washed twice for five minutes each time with the specified medium to remove any extra debris, and stored in the medium until used for the cell cultures. The cells employed for this example were primary and secondary meniscus fibroblasts obtained from sequential enzymatic digestion of whole meniscus according to the method of Cheung and Ryan (23). The medium employed for this example was DMEM supplemented with 10% HS and 1% PSF.

Figure 19:
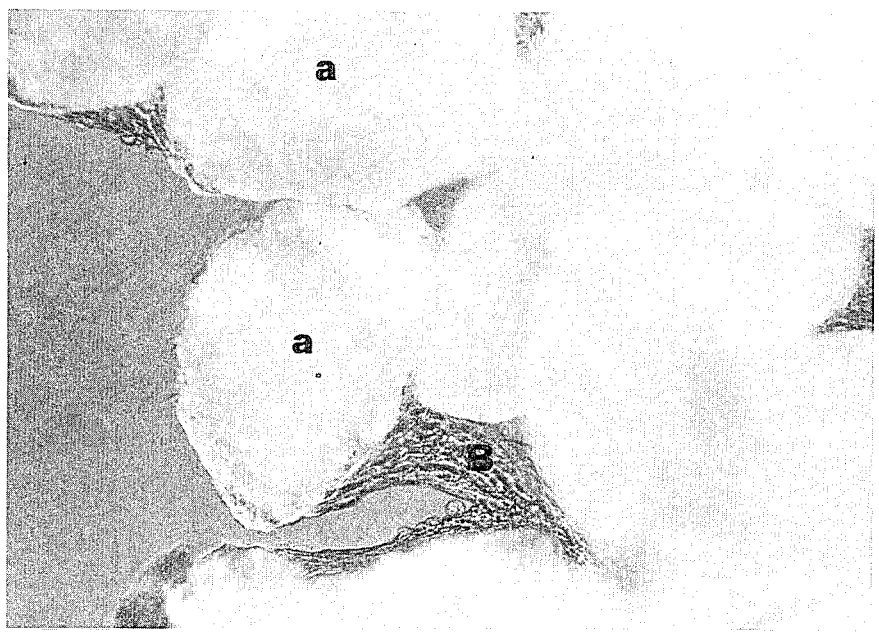
Figure 20:
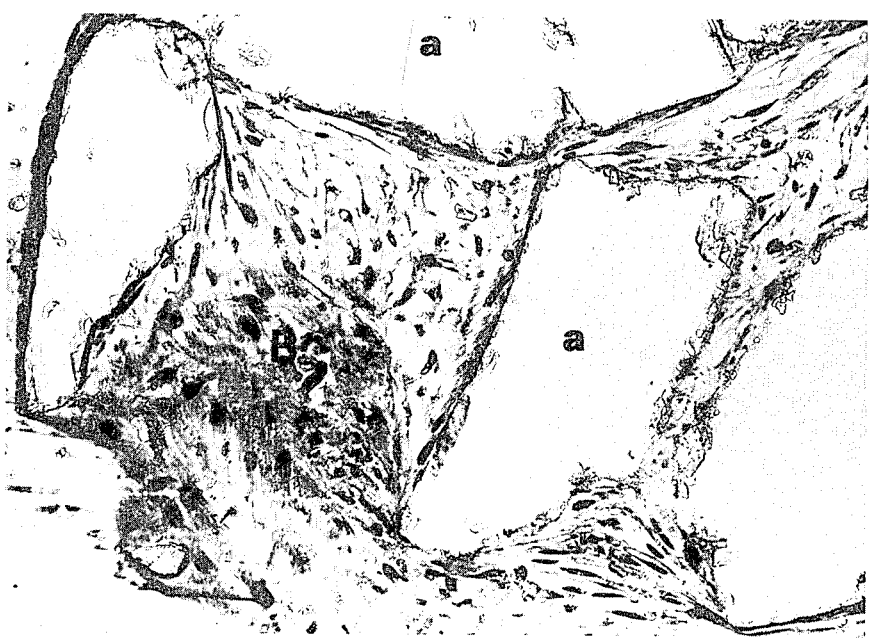
Figure 21:
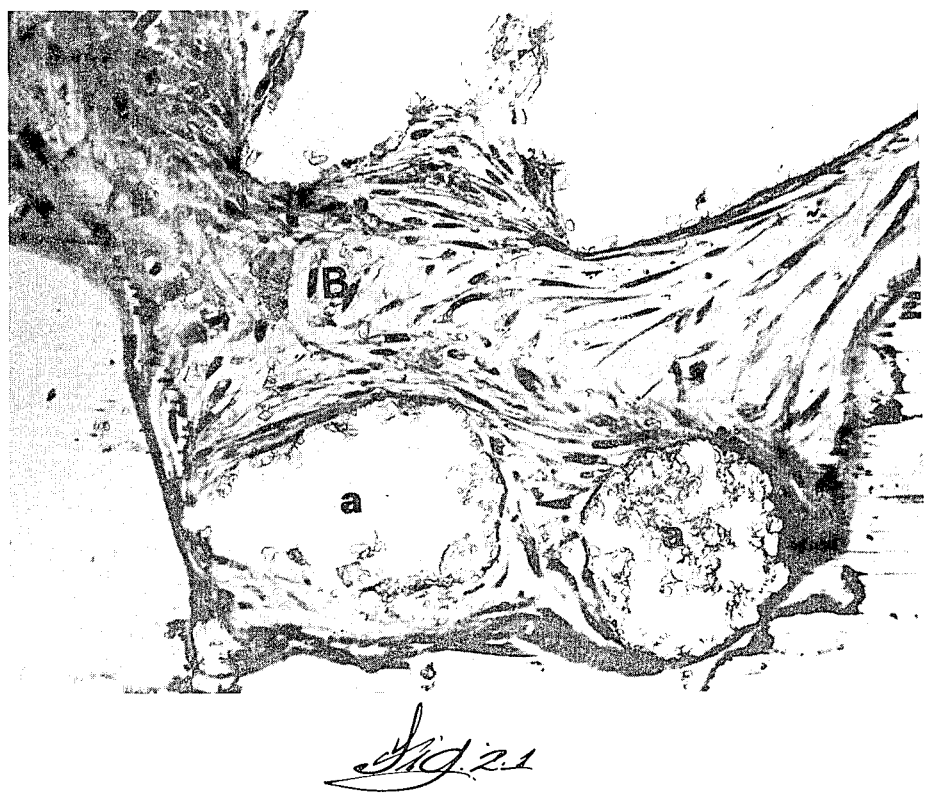

Approximately $5 \times 10^5$ cells were seeded onto about 500 to 1,000 mgs. of the calcium carbonate granules in 60 mm. by 15 mm. Petri dishes. Four ml. of growth medium were added per dish and the cultures were maintained in a $CO_2$ incubator (Forma Scientific Marietta Ohio), with replacement of medium taking place twice a week. By the end of the second week of the cell culture, the calcium carbonate granules were covered with multi-cell layers. The cultures were continued for twelve weeks, at which time they were terminated; it was observed that the multi-cell layers continued to grow throughout the twelve week term of the cultures. FIG. 19 is a light photomicrograph at 75× of a cell culture of this example taken at the end of twelve weeks in which the calcium carbonate solid substrate is shown by the reference letter A, and the multi-cell layers are shown by the reference letter B. FIGS. 20 and 21 are light photomicrographs at 125× and 150× of H and E stained sections of cell cultures of this example illustrating in further detail the multi-cell layers of cell growth.

The cell cultures of this example were examined for their ability to maintain their phenotypic expression which was determined by analyzing for proteolytic enzyme-collagenase as first described above. It was found that primary meniscus cells retained their phenotypic expression throughout the twelve weeks of culture under this example. Further, the secondary passaged meniscus cells also maintained their phenotypic expression, albeit at a reduced level of approximately 40% of that of the primary cell cultures, when tested at six weeks of culture; the secondary cells were not thusly tested after six weeks, but it is believed they continued their phenotypic expression. Production of Collagenase by canine meniscus fibroblast cell cultures of this example as compared to the same cells grown on the prior art plastic dish solid substrates are compared and summarized in Table III.

TABLE III

Production of Collagenase by Canine Meniscus Cells Grown on Different Substrates

| Cell Passage | Solid Substrate | Time | Collagenase U/$10^6$ cells/day |
|---|---|---|---|
| Primary Culture | Plastic | 2nd week | 0.9 ± 0.2 |
| | $CaCO_3$ | 2nd week | not done |
| | | 6th week | 0.6 ± 0.3 |
| | | 12th week | 1.1 ± 0.4 |
| Secondary Culture | Plastic | 2nd week | 0 |
| | $CaCO_3$ | 2nd week | 0.3 ± 0.1 |
| | | 6th week | 0.4 ± 0.2 |

CONCLUSION

The foregoing description discloses in vitro cell culture systems using new solid substrates that yield results which are highly advantageous and useful to both the scientific and business communities engaged in the use of cell culture systems.

The new solid substrates for in vitro culture of mammalian anchorage-dependent cells in accordance with this invention are to include mitogenic calcium compounds which are non-toxic to cells. The calcium compounds are used as a solid on which the anchorage-dependent cells grow in culture, and may be in the form of granules or in the form of a solid body. When in the form of granules, the calcium compound is to have a particle size of at least about 0.05 millimeters (at least about 50 microns), by which is meant that the solids have an average particle size of at least about 0.05 mm. in their largest dimension, it being understood that the particles may have an irregular or regular shape. This minimum particle size is required to provide a solid substrate with sufficient surface area to support the growth of anchorage-dependent cells. Calcium solid substrates in granular form, having a particle size range of about 0.050 mm. to 1.0 mm. have been found especially useful.

When used in the form of a solid body, the calcium solid substrate may be a disc-shaped member of any selected size such as described in Example 1. Solid bodies can be made in numerous other configurations, however, and may be made in the form of dishes, flasks or other vessels in which cells are grown with an appropriate medium. Also, the solid body can be in the form of a lining of a cell culture vessel. The solid bodies can be formed with irregular or textured surfaces to increase the surface area available for cell growth. Further, the calcium solid substrates may be used in porous or non-porous form. The presently-preferred calcium solid substrates include porous granules of the hydroxyapatite or tricalcium phosphate forms of calcium phosphate, solid bodies of porous hydroxyapatite or tricalcium phosphate forms of calcium phosphate made by compacting granules of such compounds, and non-porous granules or solid bodies of calcium carbonate.

The specific theory regarding the mechanism of the unique cell growth characteristics attained with the in vitro culture system of the present invention is not known to me at this time. However, my research work prior to this invention (31-38,42) has demonstrated that crystals of HA (less than 0.001 mm., or 1 micron, in size) and crystal clumps of HA (in the range of 0.010 to 0.02 mm., or 10 to 20 microns, in size) when added to mammalian cells grown in monolayer in vitro systems are mitogenic and act as a "competent" growth factor to stimulate cells to proliferate much like platelet derived growth factor (31,32,33) and that $^{45}$CaHa crystals added to monolayer in vitro systems are phagocytosed by canine synovial fibroblasts (34,35), human foreskin fibroblasts and monocytes (36), and murine bone cells and macrophages (37). Published research work by others relating to the effect of calcium ions in cells has shown that an increase of intracellular $Ca++$ is associated with and perhaps causes cell proliferation (39-41). A possible mechanism for the action of the calcium solid substrates of this invention, which I postulate but do not wish to be bound by at this time, is that the calcium solids are solubilized through phagocytosis of crystals followed by dissolution in the acidic environment of secondary lysosomes. The soluble nuclide would then either diffuse from or be pumped from the lysosomes into cytosol of the cells, thus raising the intracellular calcium ion $Ca++$ concentration (38) and probably cause cell proliferation (39-41). This schema is supported by the following evidence (1) $^{45}$Ca phosphate is not solubilized in conditioned media but is solubilized in the presence of cells; (2) calcium phosphate crystal aggregates are demonstrable within intracellular membrane lined vacuoles by transmission electron microscopy within 1 hour after addition to fibroblast cells (35,42); (3) the rate of physical dissolution of hydroxyapatite increases with decreasing pH (21) and cultured fibroblast cells (43,44) maintain an intralysosomal pH substantially lower than the pH of the extracellular media; and (4) two lysomotropic cations, chloroquine and ammonium, markedly inhibit crystal dissolution and selectively inhibit calcium phosphate crystal-induced mitogenic response (38). None of the research reported in the cited publication relating to the addition of calcium ions, HA crystals or HA crystal clumps (31-44) to monolayer cell cultures evidenced the multi-cell thick layer cell growth characteristic of the present invention, and it is possible that a mechanism other than as postulated above is responsible for the unique features of the present in vitro cell culture system.

The data presented in the examples establish that mitogenic calcium solid substrates of the present invention function to support cell growth in a new configuration as compared to the prior cell culture systems. Specifically, the calcium solid substrates of the present in vitro cell culture method promote cell growth as layers many cells thick, i.e. multi-cell layers, rather than the monolayer cell growth exhibited by the prior art techniques. This is believed to be the first teaching of this result for in vitro cell culture systems.

Secondly, the data of the examples further establish that cells grown on mitogenic calcium solid substrates of the present method maintain their phenotype and that phenotype expression is sustained throughout the period of cell culture. This is in contrast to the situation most often found in connection with cell growth on prior art solid substrates, in which systems the cells generally do not maintain their phenotype expression or, in the few instances where phenotype is maintained, sustain it for only a very short period of time.

Thirdly, the data of the examples establish that cell cultures utilizing calcium solid substrates of the present method can be maintained for extraordinary lengths of time, for at least as long as 13 months as reported in Example 1. The research work to date indicates that cells will continue to grow for an even longer time when cultured with the solid substrates of the present invention. This, again, is a significant advance over the short periods of time during which cells will grow with prior art substrates, as with most such prior systems the cell culture will reach confluency in as short a time as two weeks or sometimes even less.

In vitro cell cultures utilizing the calcium solid substrates of the present method are useful for any of the purposes for which cell cultures are presently utilized in both research work and commercial production. Research relating to cell structure and morphology, which are essential to the study of human diseases, both as to diagnosis and treatment, will be substantially enhanced by the researcher now having available a cell culture system in which the cells maintain their phenotype; the multi-cell thick layers of cell growth are another important factor in this connection, since the cultured cells are available as a tissue or tissue-like configuration. Also, it is presently thought that it will be possible to use tissue grown in the present cell culture systems therapeutically for tissue transplant, such as by employing cartilage cells cultured as in Example 1 in the treatment of arthritis or skin fibroblast cells cultured as in Example 9 for skin transplants. The cell culture system of this invention can be used in the production of cell products, such as metabolites, hormones, viral products, vaccines, interferons and various cell components such as nucleic acids cell membrane. In this regard, the growth of large masses of cells by reason of the multi-cell thick layers will allow increased production of cell products; further, being able to maintain the cell cultures for extended periods of time will reduce the cost of producing cell products because it will not be necessary to provide fresh cultures every 2 to 3 weeks or some other short period of time as is necessary with the typical prior art procedures. Thus, the ability of my present cell culture methods to provide for the growth of large masses of cells (multi-cell layers) that retain their phenotype and can be cultured for extended periods of time results in significant advantages in both research and commercial uses of cell culture systems.

Calcium solid substrates employed for in vitro cell culture according to the present invention can be used in any commercially available culture vessel, for example Petri dishes, flasks, roller bottles, etc. The calcium solid substrate can be either at rest or in motion in the vessel, with an appropriate medium. A wide variety of culture medium are available commercially, and any presently-used nutrient growth medium, i.e. culture medium, which supports the growth of a particular type of cell desired to be cultured can be employed with the calcium solid substrates of the present invention. The medium can be at rest in a culture vessel or circulated through the vessel. Cell growth with the present in vitro systems can be monitored by microscopic examination directly in the culture vessels; also, part of the solid substrate can be removed from the culture vessel and stained with appropriate specific dyes and then examined microscopically. Removal of cultured cells from the present calcium solid substrates, as required when subculturing or when cells are to be biochemically analyzed, can be accomplished with either chelating agents typically used in the art, such as for example 0.05% EDTA in $Ca^{3+}$, $Mg^{2+}$ free physiologic buffered saline, or protelytic enzymes, such as for example 0.01% w/v trypsin or collagenase. The procedures of cell removal and subculturing are identical to those employed in current techniques for removal in subculturing using presently known substrates. Another advantage of the present cell culture systems, however, is that subculturing can be accomplished by removal of a portion of the calcium solid substrate with cells attached and adding to fresh calcium solid substrate. This procedure has the advantage that no chemicals or mechanical devices are needed and that fewer cells are damaged in the process. For the purpose of harvesting extracellular products, the medium from the cell culture employing the present calcium solid substrates can be removed at any time during the culture and harvested for extracellular products.

The present invention has been described above in connection with certain specific embodiments. However, it is understood that modifications to the described embodiments will become apparent to those skilled in the art of cell culture and it is intended that all such non-inventive modifications of the illustrative embodiments which do not depart from the true spirit and scope of the invention are to be included within the scope of the appended claims.

LIST OF CITATIONS

1. Glacken, M. W., R. J. Fleishaker, and A. J. Sinskey. 1983. Mammalian cells in culture. Engineering principles and scale-up. *Trends in Biotechnology* 1:102–108.
2. McCoy, T. A., W. Whittle, E. Conway. 1962. Proc. Soc. Exp. Biol. 109:225.
3. Wiemann, M. C., K. McCarthy, B. Creswick, and P. Calabresi. In Vitro 19:260.
4. van Wezel, A. L. 1967. Growth of cell strains and primary cells on microcarriers in homogeneous culture. Nature 216:64–65.
5. van Wezel, A. L., in *Methods and Applications of Tissue Culture*, Academic Press, New York, 1973.
6. *Microcarrier Cell Culture, Principles and Methods*. Pharmacia Fine Chemicals A.B., 1981.
7. Hubbard, W. 1974. Physiological calcium phosphates as orthopedic biomaterials, Ph.D. Thesis, Marquette University.

8. deGroot: *Bioceramics of Calcium Phosphate,* CRC Press, Inc., 1983.
9. Klagsbrun, M. 1979. Large scale preparation of chondrocytes. *Methods Enzymol.* Academic Press. N.Y. 58:560–564.
10. Sokoloff, L. C., J. Malemud and W. T. Green, Jr. 1970. Sulfate incorporation by articular chondrocytes in monolayer culture. *Arthritis Rheum* 13:118–124
11. Srivastava, V. M. L., C. J. Malemud, and L. Sokoloff. 1974. Chondroid expression by lapine articular chondrocytes in spinner culture following monolayer growth. *Tissue Res.* 2:127–136.
12. Trippel, S. B., M. G. Ehrlich, L. Lippiello, and H. J. Mankin. 1980. Characterization of chondrocytes from bovine articular cartilage. I. Metabolic and morphological experimental studies. *J. Bone Joint Surg.* 62-A:816–820.
13. Oegema, T. R., Jr. and R. C. Thompson, Jr. 1981. Characterization of a hyaluronic acid-dermatan sulfate proteoglycan complex from dedifferentiated human chondrocyte cultures. *J. Biol. Chem.* 256:1015–1022.
14. Okayama, M., M. Pacifici, and H. Holtzer. 1976. Differences among sulfated proteoglycans synthesized in nonchondrogenic cells, presumptive chondroblasts, and chondroblasts. *Proc. Nat. Acad. Sci.* 73:3224–3228.
15. von der Mark, K. 1980. Immunological studies on collagen type transition in chondrogenesis. *Curr. Top. Dev. Biol.* 14:199–225.
16. West, C. M., R. Lanza, J. Rosenbloom, M. Lowe, H. Holtzer, and N. Avdalovic. 1979. Fibronectin alters the phenotypic properties of cultured chick embryo chondroblasts. *Cell* 17:491–501.
17. Schlitz, J. R., R. Mayne and H. Holtzer, 1973. The synthesis of collagen and glycosaminoglycans by dedifferentiated chondroblasts in culture. *Cell Differentiation* 1:97–108.
18. Mayne, R., M. S. Vail, and E. J. Miller. 1975. Analysis of changes in collagen biosynthesis that occurs when chick chondrocytes are grown in 5-bromo-2′-deoxyuridine. *Proc. Natl. Acad. Sci. USA* 72:4511–4515.
19. Mayne, R., M. S. Vail, P. M. Mayne and E. J. Miller. 1976a. The effect of embryo extract on the types of collagen synthesized by cultured chick chondrocytes. *Dev. Biol.* 54:230–240.
20. Mayne, R., M. S. Vail, P. M. Mayne and E. J. Miller. 1976b. Changes in the type of collagen synthesized as clones of chick chondrocytes grow and eventually lose division capacity. *Proc. Natl. Acad. Sci. USA* 73:1674–1678.
21. Cheung, H. S., W. Harvey, P. D. Benya, and M. E. Nimni. 1976. New collagen markers of "derepression" synthesized by rabbit articular chondrocytes in culture. *Biochem. Biophys. Res. Commun.* 68:1371–1378.
22. Benya, P. D., S. R. Padila, and M. E. Nimni. 1977. The progeny of rabbit articular chondrocytes synthesize collagen types I and III and type I trimer, but not type II. Verification by cyanogen bromide peptide analysis. *Biochemistry* 16:865–872.
23. Cheung, H. S. and L. M. Ryan. 1981. A method of determining DNA and chondrocytes content of articular cartilage. Analytical *Biochemistry* 116:93–97.
24. Miller, E. J. 1971. Isolation and characterization of cyanogen bromide peptides from the 1(II) chain of chick cartilage collagen. *Biochemistry* 10:3030–3035.
25. Lubin, R. A., G. L. Wong, and D. V. Cohn. 1976. Biochemical characterization with parathyroid hormone and calcitonin of isolated bone cells: Provisional identification of osteoclasts and osteoblasts. *Endocrinology* 99:526–534.
26. Cheung, H. S., J. T. Nicoloff, M. B. Kamiel, L. Spolter, and M. E. Nimni. 1978. Stimulation of fibroblasts biosynthetic activity by serum of patients with pretibial myxedema. *J. Invest. Dermatology.* 71:12–17.
27. Cheung, H. S., K. L. Lynch, R. P. Johnson, and B. J. Brewer. 1980. In vitro synthesis of tissue specific type II collagen by healing cartilage. *Arthritis Rheum* 23:211–219.
28. Peterkofsky, B. and R. Diegelmann. 1971. Use of a mixture of proteinase-free collagenases for the specific assay of radioactive collagen in the presence of other proteins. *Biochemistry* 10:988–994.
29. Wong, G. L., and D. V. Cohn. 1978. The effect of parathormone on the synthesis of collaginous matrix by isolated bone cells. Proceedings, Mechanisms of Localized Bone Loss. Eds. Horton, Tarpley and Davis. Special Supplement to *Calcific Tissue Abstracts* 47–59.
30. Lubin, R. A., and D. V. Cohn. 1976. Effects of parathormone and calcitonin on citrate and hyaluronate metabolism in cultured bone. *Endrocinology* 98:413–419.
31. Cheung, H. S., M. T. Stony, and D. J. McCarty. 1984. Mitogenic effects of hydroxyapatite and calcium pyrophosphate dihydrate crystals on cultured mammalian cells. *Arthritis Rheum.* 27:668–674.
32. Cheung, H. S. and D. J. McCarty. 1984. Biological effects of calcium containing crystals on synoviocytes. In *Calcium in Biological System.* Eds. R. P. Rubin, G. Weiss, and J. W. Putney, Jr. Plenum Publishing Co., N.Y.
33. Cheung, H. S. and D. J. McCarty. 1983. Calcium containing crystals can substitute for platelet derived growth factor (PDGF) in cell culture. *Arthritis Rheum.* 26:S60.
34. Evans, R. W., H. S. Cheung, and D. J. McCarty. 1983. Uptake and dissolution of calcium phosphate crystals by cultured cells. *Arthritis Rheum* 26:S60.
35. Evans, R. W., H. S. Cheung, and D. J. McCarty. 1984. Cultured canine synovial cells solubilize $^{45}$Ca labeled hydroxyapatite crystals. *Arthritis Rheum.* 27:829–832.
36. Evans, R. W., H. S. Cheung, and D. J. McCarty. Cultured human monocytes and fibroblasts solubilize calcium phosphate crystals. Calcified Tissue International (In Press).
37. Kwong, C. H., and H. S. Cheung. Solubilization of hydroxyapatite crystals by murine bone cells, macrophages and fibroblasts: Effect of PTH. Submitted for publication.
38. Cheung, H. S., and D. J. McCarty. Calcium crystal induced mitogenesis: Intracellular dissolution is essential. Submitted for publication.
39. Dulbecco. R., and J. Elkington. 1975. Induction of growth in resting fibroblastic cell cultures by. *Proc. Nat. Acad. Sci. USA* 75:1584–1588.
40. Nykforiak, C. J., R. B. Young, T. A. Phillips. 1980. Changes in intracellular distribution during the transition of fibroblasts from the proliferating to the stationary state. *Biochem. Biophys. Res. Commun.* 3:583–587.
41. Akerman, K. E. O. 1982. Transport and cell activation. *Medical Biology* 60:168–182.

42. Cheung, H. S., P. B. Halverson, and D. J. McCarty. 1982. Release of collagenase, neutral protease and prostaglandins from cultured mammalian synovial cells by hydroxyapatite and calcium pyrophosphate dihydrate crystals. *Arthritis Rheum.* 24:1338–1344.

43. Hollemans, M., R. O. Elferink, P. G. DeGroot, A. Strijland, and J. M. Tager. 1981. Accumulation of weak bases in relation to intralysosomal pH in cultured human skin fibroblasts. *Biochem. Biophys. Acta* 643:140–151.

44. Ohkuma, S., and B. Poole. 1978. Fluorescence probe measurement of the intralysosomal pH in living cells and the perturbation of pH by various agents. *Proc Natl. Acad. Sci. USA* 75:3327–3331.

I claim:

1. In a method for in vitro culture of anchorage-dependent mammalian cells on the surface of a solid substrate immersed in a nutrient growth medium, the improvement comprising:
   providing a solid substrate consisting of a calcium compound which is mitogenic and non-toxic to the anchorage dependent mammalian cells and of a size sufficient to provide support;
   seeding the cells on the solid substrate;
   adding nutrient growth medium to cover the solid substrate and the cells; and
   growing the cells on the solid substrate for a time sufficient to grow multi-cell thick layers of the cells on the solid substrate.

2. An in vitro cell culture method according to claim 1, including:
   providing the solid substrate in the form of granules of the calcium compound having a particle size of at least 0.05 millimeters in their largest dimension.

3. An in vitro cell culture method according to claim 2, wherein:
   the granules of the calcium compound have a particle size in the range of 0.050 to 1.0 millimeters.

4. An in vitro cell culture method according to claim, 1, including:
   providing the solid substrate in the form of a solid body of the calcium compound.

5. An in vitro cell culture method according to claim 4, wherein:
   the solid body is formed of sintered porous granules of the calcium compound.

6. An in vitro cell culture method according to claim 1, 2, 3, 4, or 5 wherein:
   the calcium compound is the hydroxyapatite or tri-calcium phosphate form of calcium phosphate or calcium carbonate.

7. An in vitro cell culture method according to claim 2 or 3 including:
   growing the cells on the solid substrate for a period of time in the range of 4 weeks to 13 months.

* * * * *

UNITED STATES PATENT AND TRADEMARK OFFICE
CERTIFICATE OF CORRECTION

PATENT NO. : 4,757,017
DATED : July 12, 1988
INVENTOR(S) : Cheung

It is certified that error appears in the above-identified patent and that said Letters Patent is hereby corrected as shown below:

Column 1    Insert the following as the first paragraph:

--This invention was made with government support under Federal Grants USPHS AM-26062, AM-05621, AM-18074 and 5 KO4 AM 01065-03 awarded by the National Institutes of Health. The government has certain rights in the invention.--

Signed and Sealed this

Eighth Day of June, 1993

Attest:

MICHAEL K. KIRK

Attesting Officer    Acting Commissioner of Patents and Trademarks